(12) United States Patent
Schwartz et al.

(10) Patent No.: US 7,851,590 B2
(45) Date of Patent: Dec. 14, 2010

(54) Y2 SELECTIVE RECEPTOR AGONISTS FOR THERAPEUTIC INTERVENTIONS

(75) Inventors: Thue Schwartz, Hoersholm (DK); Feng Wang, Cincinnati, OH (US)

(73) Assignee: 7TM Pharma A/S, Hoersholm (DK)

( * ) Notice: Subject to any disclaimer, the term of this patent is extended or adjusted under 35 U.S.C. 154(b) by 0 days.

(21) Appl. No.: 12/067,409

(22) PCT Filed: Sep. 21, 2005

(86) PCT No.: PCT/EP2005/010315

§ 371 (c)(1),
(2), (4) Date: Jun. 12, 2008

(87) PCT Pub. No.: WO2007/038943

PCT Pub. Date: Apr. 12, 2007

(65) Prior Publication Data

US 2008/0255046 A1    Oct. 16, 2008

(51) Int. Cl.
C07K 14/435    (2006.01)
(52) U.S. Cl. .................................. 530/324; 514/12
(58) Field of Classification Search ................. 530/324; 514/12
See application file for complete search history.

(56) References Cited

U.S. PATENT DOCUMENTS

| | | | |
|---|---|---|---|
| 5,604,203 A | 2/1997 | Balasubramaniam | |
| 5,830,434 A | 11/1998 | Taylor | |
| 6,458,381 B1 | 10/2002 | Sourovoi | |
| 6,588,708 B2 | 7/2003 | Wang | |
| 7,459,432 B2* | 12/2008 | Cowley et al. ............... | 514/12 |
| 2004/0214772 A1 | 10/2004 | Quay | |
| 2008/0255046 A1* | 10/2008 | Schwartz et al. ............. | 514/12 |
| 2008/0261871 A1 | 10/2008 | Schwartz | |
| 2008/0269114 A1 | 10/2008 | Schwartz | |
| 2009/0118178 A1 | 5/2009 | Schwartz | |
| 2009/0186811 A1* | 7/2009 | Schwartz .................... | 514/12 |

FOREIGN PATENT DOCUMENTS

| | | |
|---|---|---|
| WO | WO 92/07935 | 5/1992 |
| WO | WO 95/17906 | 7/1995 |
| WO | WO 98/11126 | 3/1998 |
| WO | WO 99/46283 | 9/1999 |
| WO | WO 02/47712 | 6/2002 |
| WO | WO 03/026591 | 4/2003 |
| WO | WO 2005/053726 | 6/2005 |
| WO | WO 2005/077094 | 8/2005 |
| WO | WO 2005/089786 | 9/2005 |
| WO | WO 2005/089789 | 9/2005 |
| WO | WO 2005/089790 | 9/2005 |
| WO | WO 2007/038942 | 4/2007 |
| WO | WO 2007/038943 | 4/2007 |
| WO | WO 2008/132435 | 11/2008 |
| WO | 2009/007714 | * 1/2009 |

OTHER PUBLICATIONS

Cabrele, C., Peptides (New York, NY, United States) 22(3), 365-378, 2001.*
McCrea, K., Regulatory Peptides 87(1-3), 47-58, 2000.*
Asakawa et al., "Characterization of the Effects of Pancreatic Polypeptide in the Regulation of Energy Balance," Gastroenterology 124, 1325-36, 2003.
Balasubramanian et al., "Syntheses and Receptor Affinities of Partial Sequences of Peptide YY (PYY)," *Peptide Res. 1*, 1988, Sep. 1988.
Bard et al., "Cloning and Functional Expression of a Human Y4 Subtype Receptor for Pancreatic Polypeptide, Neuropeptide Y, and Peptide YY," J. Biol. Chem. 270, 26762-65, Nov. 10, 1995.
Batterham et al., "Gut Hormone PYY3-36 Physiologically Inhibits Food Intake," *Nature* 418, 650-54, Aug. 8, 2003.
Batterham et al., "Pancreatic Polypeptide Reduces Appetite and Food Intake in Humans," *J. Clin. Endocrinol. Metab. 88*, 3989-92, Aug. 2003.
Berntson et al., "Pancreatic Polypeptide Infusions Reduce Food Intake in Prader-Willi Syndrome," *Peptides 14*, 4970503, 1993.
Dumont et al., "Characterization of a new neuropeptide Y Y5 agonist radioligand: [<125>I][cPP(1-7), NYP(19-23), Ala<31>, Aib<32>, Gln<34>]hPP," Neuropeptides, vol. 38, No. 4, pp. 163-174, Aug. 2004.
Eberlein et al., "A New Molecular Form of PYY: Structural Characterization of Human PYY (3-36) and PYY (1-36)," *Peptides 10*, 797-803, 1989.
Félétou Michel et al., "Neuropeptide Y2 receptors as drug targets for the central regulation of body weight," Current Opinion in Investigational Drugs, vol. 6, No. 10, pp. 1002-1011, Oct. 2005.
Fuhlendorff J et al: "The anti parallel pancreatic polypeptide fold in the binding of neuropeptide Y to Y-1 and Y-2 receptors" Jul. 15, 1990, Journal of Biological Chemistry, American Society of Biological Chemists, Baltimore, MD, US, pp. 11706-11712, XPQ02339077 ISSN: 0021-9258.
Gehlert et al., "Characterization of the Peptide Binding Requirements for the Cloned Human Pancreatic Polypeptide-Preferring Receptor," *Mol. Pharmacol. 50i*, 112-18, 1996.
Gerald et al., "Expression Cloning and Pharmacological Characterization of a Human Hippocampal Neuropeptide Y/Peptide YY Y2 Receptor Subtype," J. Biol. Chem. 270, 26758-61, 1995.
Grundemar, "Characterization of the Receptor Response for the Neuropeptide Y-Evoked Suppression of Parasympathetically-Mediated Contractions in the Guinea Pig Trachea," *Regulatory Peptides 71*, 97-101, 1997.

(Continued)

*Primary Examiner*—David Lukton
(74) *Attorney, Agent, or Firm*—Banner & Witcoff, Ltd.

(57) ABSTRACT

The modified human PP peptides (i) [Lys4,Leu17,Ser30, Gln34]hPP, (ii) Lys4,Leu17,Thr30,Gln34]hPP; and (iii) [Lys4,Leu17,oxidised Met30,Gln34]hPP wherein "oxidised Met" may be the sulfoxide or sulfone, and certain analogues and derivatised forms thereof as referred to in the specification, are selective agonists of the Y2 receptor relative to the Y1 and Y4 receptors, and are useful for, for example, appetite control and therapeutic angiogenesis.

37 Claims, No Drawings

OTHER PUBLICATIONS

Jorgensen et al., "Structure-function studies on neuropeptide Y and pancreatic polypeptide: Evidence for two PP-fold receptors in vas deferens," Eur. J. Pharmacol. 186, 105-14, 1990.

Katsuura et al., "Roles of Pancreatic Polypeptide in Regulation of Food Intake," *Peptides 23*, 323-29, 2002.

Keire et al., "Structure and receptor binding of PYY analogs," Peptides, vol. 23, No. 2, pp. 305-321, Feb. 2002.

Kirby et al., "Defining Structural Requirements for Neuropeptide Y Receptors Using Truncated and Conformationally Restricted Analogues," *J. Med. Chem. 36*, 385-93, 1993.

Kurtzhals et al., "Albumin Binding of Insulins Acylated with Fatty Acids: Characterization of the Ligand-Protein Interaction and Correlation between Binding Affinity and Timing of the Insulin Effect in Vivo," Biochemical Journal, vol. 312, No. 3, pp. 725-731, 1995.

Larsen et al., "The Neuropeptide Y_Y4/ Receptor is Highly Expressed in Neurones of the Rat Dorsal Vagal Complex," *Mol. Brain Res. 48*, 1-6, 1997.

Lerch et al., "Bovine Pancreatic Polypeptide (bPP) Undergoes Significant Changes in Conformation and Dynamics upon Binding to DPC Micelles," *J. Mol. Biol. 322*, 1117-33, 2002.

Lerch et al., "Structural Similarities of Micelle-bound Peptide YY (PYY) and Neuropeptide Y (NPY) are Related to their Affinity Profiles at the Y Receptors," *J. Mol. Biol. 339*, 1153-68, Jun. 18, 2004.

Medeiros & Turner, "Post-Secretory Processing of Regulatory Peptides: The Pancreatic Polypeptide Family as a Model Example," Biochemie 76, 283-87, 1994.

Murase Sachiko et al., "Acylation of the α Group in Neuropeptide Y(12-36) Increases Binding Affinity for the $Y_2$ Receptor," *Abstr. J. Biochem* (Tokyo) 119, 37-41, 1996.

Nygaard et al., "The PP-Fold Solution Structure of Human Polypeptide YY and Human PYY3-36 as Determined by NMR," *Biochem. 45*, 8350-57, 2006.

Parker et al., "GR231118 (1229U91) and other analogs of the C-terminus of neuropeptide Y are potent neuropeptide Y Y1 receptor antagonists and neuropeptide Y Y4 receptor agonists," Eur. J. Pharmacol. 349, 97-105, 1998.

Rossi et al., "Central nerous system neuropeptides involved in obesity," Handbook of Exp. Pharmacol. 149, 313-41, 2000.

Sheffield, "Modification of clearance of therapeutic and potentially therapeutic proteins," Cardiovascular and Haematological Disorders, vol. 1, No. 1, pp. 1-22, Jun. 2001.

Walker et al., "A Structure-Activity Analysis of the Cloned Rat and Human Y4 Receptors for Pancreatic Polypeptide[1,2]," *Peptides 18*, 609-12, 1997.

Walker et al., "Peptide Receptor Structure and Function I," *Soc. Neuroscience Abs. 21*, 1012, Nov. 11, 1995.

Walker et al., "Binding of NPY8 PYY and PP Analogs to cloned human Y2 and Y4 receptors" Society for Neuroscience Abstracts, Society for Neuroscience, US, vol. 21, No. 1/3 Nov. 11, 1995.

UnitProt Accession No. P01298, Apr. 3, 2007.

U.S. Appl. No. 12/597,090, filed Oct. 22, 2009 (unpublished).

Yao Shenggen et al., "Stabilization of the Helical Structure of Y2-Selective Analogues of Neuropeptide Y by Lactam Bridges," *J. Med. Chem. 45*, 2310-18, May 23, 2002.

\* cited by examiner

SEQUENCE LISTING

<160> NUMBER OF SEQ ID NOS: 14

<210> SEQ ID NO 1
<211> LENGTH: 36
<212> TYPE: PRT
<213> ORGANISM: Homo sapiens
<220> FEATURE:
<223> OTHER INFORMATION: Y2 receptor agonist

<400> SEQUENCE: 1

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

-continued

<210> SEQ ID NO 2
<211> LENGTH: 36
<212> TYPE: PRT
<213> ORGANISM: Homo sapiens
<220> FEATURE:
<223> OTHER INFORMATION: Y2 receptor agonist

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 36
<212> TYPE: PRT
<213> ORGANISM: Homo sapiens
<220> FEATURE:
<223> OTHER INFORMATION: Y2 receptor agonist

<400> SEQUENCE: 3

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 4
<211> LENGTH: 36
<212> TYPE: PRT
<213> ORGANISM: Artificial Sequence
<220> FEATURE:
<223> OTHER INFORMATION: Y2 receptor agonist

<400> SEQUENCE: 4

Ala Pro Leu Lys Pro Val Tyr Pro Gly Asp Asn Ala Thr Pro Glu Gln
1               5                   10                  15

Leu Ala Gln Tyr Ala Ala Asp Leu Arg Arg Tyr Ile Asn Ser Leu Thr
            20                  25                  30

Arg Gln Arg Tyr
        35

<210> SEQ ID NO 5
<211> LENGTH: 36
<212> TYPE: PRT
<213> ORGANISM: Artificial Sequence
<220> FEATURE:
<223> OTHER INFORMATION: Y2 receptor agonist

<400> SEQUENCE: 5

Ala Pro Leu Lys Pro Val Tyr Pro Gly Asp Asn Ala Thr Pro Glu Gln
1               5                   10                  15

Leu Ala Gln Tyr Ala Ala Asp Leu Arg Arg Tyr Ile Asn Thr Leu Thr
            20                  25                  30

Arg Gln Arg Tyr
        35

<210> SEQ ID NO 6

```
<211> LENGTH: 36
<212> TYPE: PRT
<213> ORGANISM: Artificial Sequence
<220> FEATURE:
<223> OTHER INFORMATION: Y2 receptor agonist

<400> SEQUENCE: 6

Ala Pro Leu Lys Pro Val Tyr Pro Gly Asp Asn Ala Thr Pro Glu Gln
 1               5                  10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 7
<211> LENGTH: 16
<212> TYPE: PRT
<213> ORGANISM: Artificial Sequence
<220> FEATURE:
<223> OTHER INFORMATION: GAG binding motif

<400> SEQUENCE: 7

Ala Arg Arg Arg Ala Ala Arg Ala Ala Arg Arg Arg Ala Ala Arg Ala
 1               5                  10                  15

<210> SEQ ID NO 8
<211> LENGTH: 24
<212> TYPE: PRT
<213> ORGANISM: Artificial Sequence
<220> FEATURE:
<223> OTHER INFORMATION: GAG binding motif

<400> SEQUENCE: 8

Ala Arg Arg Arg Ala Ala Arg Ala Ala Arg Arg Arg Ala Ala Arg Ala
 1               5                  10                  15

Ala Arg Arg Arg Ala Ala Arg Ala
            20

<210> SEQ ID NO 9
<211> LENGTH: 8
<212> TYPE: PRT
<213> ORGANISM: Artificial Sequence
<220> FEATURE:
<223> OTHER INFORMATION: GAG binding motif

<400> SEQUENCE: 9

Ala Arg Arg Arg Ala Ala Arg Ala
 1               5

<210> SEQ ID NO 10
<211> LENGTH: 27
<212> TYPE: PRT
<213> ORGANISM: Artificial Sequence
<220> FEATURE:
<223> OTHER INFORMATION: GAG binding motif

<400> SEQUENCE: 10

Ala Arg Arg Arg Ala Ala Ala Arg Ala Ala Arg Arg Arg Ala Ala Ala
 1               5                  10                  15

Arg Ala Ala Arg Arg Arg Ala Ala Ala Arg Ala
            20                  25

<210> SEQ ID NO 11
<211> LENGTH: 42
<212> TYPE: PRT
```

```
<213> ORGANISM: Artificial Sequence
<220> FEATURE:
<223> OTHER INFORMATION: Y2 receptor agonist

<400> SEQUENCE: 11

Lys Lys Lys Lys Lys Lys Ala Pro Leu Lys Pro Val Tyr Pro Gly Asp
 1               5                  10                  15

Asn Ala Leu Pro Glu Gln Met Ala Gln Tyr Ala Ala Asp Leu Arg Arg
            20                  25                  30

Tyr Ile Asn Ser Leu Thr Arg Gln Arg Tyr
        35                  40

<210> SEQ ID NO 12
<211> LENGTH: 7
<212> TYPE: PRT
<213> ORGANISM: Artificial Sequence
<220> FEATURE:
<223> OTHER INFORMATION: helix-inducing peptide

<400> SEQUENCE: 12

Lys Lys Lys Lys Lys Lys Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: GAG  binding motif
<221> NAME/KEY: VARIANT
<222> LOCATION: 1, 4, 6
<223> OTHER INFORMATION: Xaa = Any Amino Acid
<221> NAME/KEY: VARIANT
<222> LOCATION: 2, 3, 5
<223> OTHER INFORMATION: Xaa = basic amino acid
<221> NAME/KEY: VARIANT
<222> LOCATION: (1)...(6)
<223> OTHER INFORMATION: Xaa = Any Amino Acid

<400> SEQUENCE: 13

Xaa Xaa Xaa Xaa Xaa Xaa
 1               5

<210> SEQ ID NO 14
<211> LENGTH: 8
<212> TYPE: PRT
<213> ORGANISM: Artificial Sequence
<220> FEATURE:
<223> OTHER INFORMATION: GAG binding motif
<221> NAME/KEY: VARIANT
<222> LOCATION: 1, 5, 6, 8
<223> OTHER INFORMATION: Xaa = Any Amino Acid
<223> OTHER INFORMATION: Xaa = basic amino acid
<221> NAME/KEY: VARIANT
<222> LOCATION: (1)...(8)
<223> OTHER INFORMATION: Xaa = Any Amino Acid

<400> SEQUENCE: 14

Xaa Xaa Xaa Xaa Xaa Xaa Xaa Xaa
 1               5
```

Y2 SELECTIVE RECEPTOR AGONISTS FOR THERAPEUTIC INTERVENTIONS

CROSS REFERENCE TO RELATED APPLICATIONS

This application is a National Stage application of co-pending PCT application PCT/EP2005/010315 filed Sep. 21, 2005, which is incorporated herein by reference in its entirety.

This application incorporates by reference the contents of a 4.95 KB text file created on Nov. 23, 2009 and named "SN12067409_sequencelisting.txt," which is the sequence listing for this application.

FIELD OF THE INVENTION

The invention relates to peptide or peptidic compounds that act as selective agonists of the Y2 relative to the Y1 and Y4 receptors, and to their use in treatment of conditions responsive to activation of Y2 receptors, for example in treatment of obesity and overweight, and conditions in which these are considered contributory factors, and for induction of angiogenesis.

BACKGROUND TO THE INVENTION

The PP-fold family of peptides—NPY (Neuropeptide Y) (human sequence—SEQ ID. No:1), PYY (Peptide YY) (human sequence—SEQ ID. No:2), and PP (Pancreatic Polypeptide) (human sequence—SEQ ID. No:3), are naturally secreted homologous, 36 amino acid, C-terminally amidated peptides, which are characterized by a common three-dimensional, structure—the PP-fold—which is surprisingly stable even in dilute aqueous solution and is important for the receptor recognition of the peptides.

NPY is a very wide-spread neuropeptide with multiple actions in various parts of both the central and peripheral nervous system acting through a number of different receptor subtypes in man: Y1, Y2, Y4 and Y5. The main NPY receptors are the Y1 receptor, which generally is the post-synaptic receptor conveying the "action" of the NPY neurones and the Y2 receptor which generally is a pre-synaptic, inhibitory receptor. This is also the case in the hypothalamus, where NPY neurones—which also express the melanocortin receptor antagonist/inverse agonist AgRP (agouti related peptide)—act as the primary "sensory" neurones in the stimulatory branch of the arcuate nucleus. Thus, in this the "sensor nucleus" for the control of appetite and energy expenditure, the NPY/AgRP neurones together with the inhibitory POMC/CART neurones monitor the hormonal and nutritional status of the body as these neurones are the target for both the long-term regulators such as leptin and insulin and short term regulators such as ghrelin and PYY (see below). The stimulatory NPY/AgRP neurones project for example to the paraventricular nucleus—also of the hypothalamus—where its postsynaptic target receptors are believed to be Y1 and Y5 receptors. NPY is the most potent compound known in respect of increasing food intake, as rodents upon intracerebroventricular (ICV) injection of NPY will eat until they literally burst. AgRP from the NPY/AgRP neurones acts as an antagonist mainly on melanocortin receptors type 4 (MC-4) and block the action of POMC derived peptides—mainly aMSH—on this receptor. Since the MC4 receptor signal acts as an inhibitor of food intake, the action of AgRP is—just like the NPY action—a stimulatory signal for food intake (i.e. an inhibition of an inhibition). On the NPY/AGRP neurons are found inhibitory—pre-synaptic—Y2 receptors, which are the target both of locally released NPY as well as a target for the gut hormone PYY—another PP-fold peptide.

PYY is released during a meal—in proportion to the calorie content of the meal—from entero-endocrine cells in the distal small intestine and the colon, to act both in the periphery on GI-tract functions and centrally as a satiety signal. Peripherally, PYY is believed to function as an inhibitor—an "illeal break"—on for example upper GI-tract motility, gastric acid and exocrine pancreatic secretion. Centrally, PYY is believed to act mainly on the presynaptic, inhibitory Y2 receptors on the NPY/AgRP neurones in the arcuate nucleus, which it is believed to get access to from the blood (Batterham et al. 2002 *Nature* 418: 650-4). The peptide is released as PYY1-36, but a fraction—approximately 50%—circulates as PYY3-36 which is a product of degradation by dipeptidylpeptidase-IV an enzyme which removes a dipeptide from the N-terminus of a peptide provided that a Pro or Ala is found in position two as in all three PP-fold peptides—PP, PYY and NPY (Eberlein et al. 1989 *Peptides* 10: 797-803). Thus PYY in the circulation is a mixture of PYY1-36, which acts on both Y1 and Y2 receptors (as well as Y4 and Y5 with various affinities), and PYY3-36—which has lower affinities for the Y1, Y4 and Y5 receptors than for the Y2 receptor.

PP is a hormone, which is released from endocrine cells in the pancreatic islets, almost exclusively governed by vagal cholinergic stimuli elicited by especially food intake (Schwartz 1983 *Gastroenterology* 85:1411-25). PP has various effects on the gastrointestinal tract, but most of these are not observed in isolated cells and organs, and appear to be dependent on an intact vagal nerve supply (Schwartz 1983 *Gastroenterology* 85:1411-25). In accordance with this, the PP receptors, which are called Y4 receptors, are located in the brain stem with a strong expression in vagal motor neurones—activation of which results in the peripheral effects of PP—and in the nucleus tractus solitarirus (NTS)—activation of which results in the effects of PP as a satiety hormone (Whitecomb et al. 1990 *Am. J. Physiol.* 259: G687-91, Larsen & Kristensen 1997 *Brain Res. Mol. Brain Res* 48: 1-6). It should be noted that PP from the blood has access to this area of the brain since the blood brain barrier is "leaky" in this area where various hormones from the periphery are sensed. Recently it has been argued that part of the effect of PP on food intake is mediated through an action on neurones—especially the POMC/CART neurones in the arcuate nucleus (Batterham et al. 2004 *Abstract* 3.3 *International NPY Symposium* in Coimbra, Portugal). PP acts through Y4 receptors for which it has a subnanomolar affinity as opposed to PYY and NPY which have nanomolar affinity for this receptor (Michel et al. 1998 *Pharmacol. Rev.* 50: 143-150). PP also has an appreciable affinity for the Y5 receptor, but it is not likely of physiological importance in relation to circulating PP due to both lack of access to the cells in the CNS where this receptor especially is expressed and due to the relatively low affinity for PP.

PP-Fold Peptide Receptors

There are four well established types of PP-fold peptide receptors in man: Y1, Y2, Y4, and Y5 which all recognize NPY and PYY with similar affinity. At one time a Y3 receptor type, which might prefer NPY over PYY, was suggested, but today this is not accepted as a real receptor subtype (Michel et al. 1998 *Pharmacol. Rev.* 50: 143-150). A Y6 receptor subtype has been cloned, however in man this is expressed in a truncated form lacking TM-VII as well as the receptor tail and consequently at least on its own does not appear to form a functional receptor molecule.

Y1 receptors—affinity studies suggest Y1 binds NPY and PYY equally well and basically not PP.

Y2 receptors—affinity studies suggest Y2 binds NPY and PYY equally well and basically not PP.

Y4 receptors—affinity studies suggest that Y4 binds PP with subnanomolar affinity corresponding to the concentrations found in plasma whereas NPY and PYY are recognized with much lower affinity.

Y5 receptors—affinity studies suggest that Y5 binds NPY and PYY equally well, and also binds PP with lower affinity, which however is below the normal circulating levels of this hormone. PYY3-36 is also recognized well by the Y5 receptor. However this receptor is to a large degree expressed in the CNS where PYY3-36 cannot get access to the receptor readily when administered in the periphery.

PP-fold peptides and analogs of these have been suggested for use in the treatment of obesity and associated diseases, including for example Prader Willi's syndrome, based on the demonstrated effects of certain of the these peptides in animal models and in man and on the fact that obese people have low basal levels of PYY and PP as well as lower meal responses of these peptides (Holst J J et al. 1983 *Int. J. Obes.* 7: 529-38; Batterham et al. 1990 *Nature*). Infusion of PP in patients with Prader Willi's syndrome was early on shown to decrease food intake (Berntson et al. 1993 *Peptides* 14: 497-503) and this effect has been confirmed by infusion of PP in normal human subjects (Batterham et al 2003, *Clin. Endocrinol. Metab.* 88: 3989-92). PP-fold peptides have also been suggested for the use in for example therapeutic angiogenesis (Zukowska et al. 2003 *Trends Cardiovasc Med.* 13:86-92) and in inflammatory bowl disease (see for example WO 03/105763).

For the treatment of conditions responsive to Y receptor modulation, it would therefore be desirable to use Y receptor PP-fold peptides or PP-fold peptide mimics which were specific for the selected Y receptor intended as target, and which stably preserve elements of the PP-fold structure important for receptor binding. In particular, it would be highly desirable to use such agents which are selective for the Y2 receptor over the Y1 and Y4 receptors. The Y2 receptor is the receptor, which will give the beneficial effect on for example food intake and energy expenditure for the treatment of obesity, metabolic syndrome etc. and it is also the Y2 receptor which will give the beneficial effect to obtain therapeutic angiogenesis in patients with for example peripheral vascular disease or coronary vascular disease. However, an agent which acts as a Y2 receptor agonist is not particularly useful for such treatment unless it is selective for the Y2 receptor over the Y1 and the Y4 receptors. Agonism on the Y1 receptor will, for example induce serious side effects in the cardiovascular system—increase in blood pressure—as well as renal system—natriuresis. Similarly, Y2 selectivity over the Y4 receptor is desirable, since the two natural Y2 and Y4 agonists, PYY and PP respectively, have many similar effects on for example the gastrointestinal tract—some of which could be beneficial—but some of which may cause unwanted side effects. For example, both Y2 and Y4 receptors promote antisecretory effects in the small and large intestine through respectively a neuronal and a direct epithelial mode of action (Cox et al. 2002 *Br. J. Pharmacol.* 135: 1505-12). Thus, it is likely that an additive or even possibly a synergistic antisecretory effect would be obtained through a combined stimulation of the Y2 and the Y4 receptor, which could lead to constipation.

Our co-pending International patent application no PCT/EP2005/002981, the contents of which are hereby incorporated by reference, relates to a class of Y receptor agonists which are selective for the Y2 receptor over the Y1 and Y4 receptors, and to some specific members of that class.

This invention relates to specific peptides which are highly selective for the Y2 receptor over the Y1 and Y4 receptors.

DETAILED DESCRIPTION OF THE INVENTION

According to the invention, there is provided a peptide selected from the group consisting of (i)    [Lys4, Leu17, Ser30, Gln34]hPP,    (SEQ ID No: 4)

(ii)   [Lys4, Leu17, Thr30, Gln34]hPP;    (SEQ ID No: 5)

(iii)  [Lys4, Leu17, oxidized Met30, Gln34]hPP;   (SEQ ID No: 6)

and analogues of (i), (ii) or (iii) which are (a) conservatively substituted in one or more positions other than positions 4, 17, 30 and 34 and/or (b) N-terminally acylated, PEGylated, or covalently coupled to a serum albumin binding motif, a glycosaminoglycan binding motif or a helix inducing motif, said covalent coupling being to a residue of peptide (i), (ii) or (iii) or to a residue substituted in peptide (i), (ii) or (iii) which provides a functional group for such covalent binding.

The notation hPP used herein refers to the human PP sequence, SEQ ID No:3. Thus, the peptide [Lys4,Leu17, Ser30,Gln34]hPP has the human PP sequence SEQ ID No:3, but with lysine substituted at position 4, leucine substituted at position 17, serine substituted at position 30 and glutamine substituted at position 34. The notation "oxidised Met" refers to a methionine residue wherein the sulfur atom of the side chain methylthio group is oxidised to a sulfoxide (one oxygen) or a sulfone (two oxygens). In one embodiment of the invention the oxidised Met30 in peptide (iii) of the invention is a sulfoxide.

The three peptides and their analogues of the invention are Y receptor agonists which are highly selective for the Y2 receptor over the Y1 and Y4 receptors when measured by the affinity and/or potency assays described herein.

In this specification, reference is made to amino acids by their common names or abbreviations, such as valine (Val), leucine (Leu), isoleucine (Ile), methionine (Met), phenylalanine (Phe), asparagine (Asn), glutamic acid (Glu), glutamine (Gln), histidine (His), lysine (Lys), arginine (Arg), aspartic acid (Asp), glycine (Gly), alanine (Ala), serine (Ser), threonine (Thr), tyrosine (Tyr), tryptophane (Trp), cysteine (Cys) and proline (Pro). When referred to by its common name or abbreviation, without specifying its stereoisomeric form, the amino acid in question is to be understood as the L-form. Where the D-form is intended, the amino acid will be specifically referred to as such. Occasionally, where the context makes it desirable to do so, the L-form will be specified rather than inferred.

Conservatively Substituted Analogues

The term "conservatively substituted" as used herein denotes that one or more amino acids is replaced by another, biologically similar residue. Examples include substitution of amino acid residues with similar characteristics, e.g. small amino acids, acidic amino acids, polar amino acids, basic amino acids, hydrophobic amino acids and aromatic amino acids. Non-limiting examples of conservative amino acid substitutions suitable for use in the present invention include those in the following Table and analogous substitutions of the original residue by non-natural alpha amino acids which have similar characteristics. An example of a conservative substitution with a residue normally not found in endogenous, mammalian peptides and proteins would be the conservative substitution of Arg or Lys with for example, ornithine, canavanine, aminoethylcysteine or other basic amino acid. For further information concerning phenotypically silent substitutions in peptides and proteins, see, for example, Bowie et. al. *Science* 247, 1306-1310, 1990.

| Original residue | Conservative substitution |
|---|---|
| Ala | Gly |
| Arg | Lys |
| Asn | Gln, His, Thr |
| Asp | Glu |
| Gln | Asn, His |
| Glu | Asp |
| His | Asn, Gln |
| Ile | Leu, Val |
| Leu | Ile, Val |
| Lys | Arg |
| Met | Leu, Ile |
| Phe | Tyr, Trp, His |
| Ser | Thr, Asn |
| Thr | Ser, Asn, Gln |
| Trp | Tyr, Phe, His |
| Tyr | Trp, Phe, His |
| Val | Ile, Leu |

Conservatively substituted analogues of the invention may have, for example, up to 10 conservative substitutions, or in another embodiment up to 5, or in yet another embodiment 3 or fewer.

N-Acylated Analogues

All three Y2 selective agonists with which the invention is concerned may be acylated at their N-terminus to confer resistance to aminopeptidase activity. For example acylation may be with a carbon chain having from 2 to 24 carbon atoms, and N-terminal acetylation is a particular example.

Analogues with Covalently Bound Functional Motifs

Various modifications may be made to the three agonists of the invention, for the purpose of improving their pharmacokinetics, pharmacodynamics and metabolic properties. Such modifications may involve linking the agonist to functional groupings (also known as motifs) known per se in the art of peptidic or proteinaceous pharmaceuticals. Three particular modifications of particular benefit in the case of the agonists with which the invention is concerned, are linkage with serum albumin binding motifs, or glycosaminoglycan (GAG) binding motifs, or PEGylation.

Serum-Albumin Binding Motifs

Serum albumin binding motifs are typically lipophilic groups, incorporated to enable a prolonged residence in the body upon administration or for other reasons, which may be coupled in various known ways to peptidic or proteinaceous molecules, for example i) via a covalent linkage to e.g. a functional group present on a side-chain amino acid residue, ii) via a functional group inserted in the peptide or in a suitable derivatized peptide, iii) as an integrated part of the peptide. For example, WO 96/29344 (Novo Nordisk A/S) and P. Kurtzhals et al. 1995 Biochemical J. 312: 725-31 and L. B. Knudsen et al. 2000 J. Med. Chem. 43:1664-69, describe a number of suitable lipophilic modifications which can be employed in the case of the agonists with which this invention is concerned.

Suitable lipophilic groups include optionally substituted, saturated or unsaturated, straight or branched hydrocarbon groups of from 10 to 24 carbon atoms. Such groups may form, or may form part of, a side chain to the backbone of the agonist, for example by ether, thioether, amino, ester or amide linkage to a side chain of an amino acid residue in the backbone, or to a backbone carbon or a branch from a backbone carbon of a non-peptidic linker radical in the backbone of a PP-fold mimic agonist. The chemistry strategy for attachment of the lipophilic group is not critical, but the following side chains including lipophilic groups are examples which can be linked to a backbone carbon of the agonist, or suitable branch therefrom:

$CH_3(CH_2)_n CH(COOH)NH—CO(CH_2)_2 CONH—$ wherein n is an integer from 9 to 15, $CH_3(CH_2)_r CO—NHCH(COOH)(CH_2)_2 CONH—$ wherein r is an integer form 9 to 15, $CH_3(CH_2)_s CO—NHCH((CH_2)_2 COOH)CONH—$ wherein s is an integer from 9 to 15, $CH_3(CH_2)_m CONH—$, wherein m is an integer from 8 to 18, $—NHCOCH((CH_2)_2 COOH)NH—CO(CH_2)_p CH_3$, wherein p is an integer from 10 to 16, $—NHCO(CH_2)_2 CH(COOH)NH—CO(CH_2)_q CH_3$, wherein q is an integer from 10 to 16, $CH_3(CH_2)_n CH(COOH)NHCO—$, wherein n is an integer from 9 to 15, $CH_3(CH_2)_p NHCO—$, wherein p is an integer from 10 to 18, $—CONHCH(COOH)(CH_2)_4 NH—CO(CH_2)_m CH_3$, wherein m is an integer from 8 to 18, $—CONHCH(COOH)(CH_2)_4 NH—COCH((CH_2)_2 COOH)NH—CO(CH_2)_p CH_3$, wherein p is an integer from 10 to 16, $—CONHCH(COOH)(CH_2)_4 NH—CO(CH_2)_2 CH(COOH)NH—CO(CH_2)_q CH_3$, wherein q is an integer from 10 to 16, and a partly or completely hydrogenated cyclopentanophenanthrene skeleton.

In one chemical synthetic strategy the lipophilic group-containing side chain is a $C_{12}$, $C_{14}$, $C_{16}$ or $C_{18}$ acyl group, for example a tetradecanoyl group, acylating an amino group present in the side chain of a residue of the backbone of the agonist.

As stated, the modification of agonists for use in accordance to provide improved serum binding characteristics is a strategy which may be applied in general, and particularly in the case of the specific agonists listed above. Thus, suitable modified agonists include [Lys4,N-(N'-tetradecanoyl)-gammagluatamoyl-Lys13,Leu17,Ser30,Gln34]PP or [Lys4,N-(N'-hexadecanoyl)-gammagluatamoyl-Lys13,Leu17,Thr30,Gln34]PP and conservatively substituted analogues thereof.

GAG Binding

As in the case of lipophilic serum binding motifs discussed above, the agonists with which this invention are concerned may be modified by incorporation of the GAG binding motif as, or as part of, a side chain to the backbone of the agonist. Known GAG-binding motifs for incorporation in this way include the amino acid sequences XBBXBX (SEQ ID NO:13) and/or XBBBXXBX (SEQ ID NO:14), wherein B is a basic amino acid residue and X is any amino acid residue. A plurality, for example three, of such sequences may be incorporated in a concatameric (straight chain) or dendrimeric (branched chain) fashion. Specific concatameric GAG motifs include Ala-Arg-Arg-Arg-Ala-Ala-Arg-Ala-Ala-Arg-Arg-Arg-Ala-Ala-Arg-Ala (SEQ ID NO:7), and Ala-Arg-Arg-Arg-Ala-Ala-Arg-Ala-Ala-Arg-Arg-Arg-Ala-Ala-Arg-Arg-Arg-Ala-Ala-Arg-Ala (SEQ ID NO:8) (both of which may, for example be coupled through an amide bond formed between the C-terminus of the concatameric GAG-binding motif and an amino group in the side chain of a backbone amino acid of the agonist, such as the epsilon amino group of Lys13 in the agonist [Lys13,Ala30]PP2-36 or [Glu10,Lys13,Leu17,Thr30]PP2-36.

Instead of being attached to the agonist as, or as part of a side chain to a backbone residue, the GAG motif may be covalently linked to the C- or (preferably) N-terminus of the agonist, either directly or via a linker radical. Here also the GAG-binding motif may comprise the amino acid sequence XBBXBX (SEQ ID NO:13) and/or XBBBXXBX (SEQ ID NO:14), wherein B is a basic amino acid residue and X is any amino acid residue, for example the sequence [XBBBXXBX (SEQ ID NO:14)]n where n is 1 to 5, B is a basic amino acid residue and X is any amino acid residue.

The Y2 selective agonists with which the present invention is concerned are useful, inter alia, for therapeutic angiogenesis. For this use in particular, the agonists preferably comprise a glycosaminoglycan (GAG) binding motif as discussed above. Such motifs ensure that the agonists bind to GAGs in the extracellular matrix, and thereby ensures prolonged local exposure of the Y2 receptors in that tissue. Growth factors, chemokines etc bind to GAGs through patches of basic amino acids, which interact with the acidic sugars of the GAGs. These positively charged epitopes on the growth factors are usually composed of side chains from basic residues, which are not necessarily located consecutively in sequence but are often presented in close proximity by a secondary structural element such as an a-helix or a turn or by the overall three dimensional structure of the protein. Certain GAG-binding, linear sequences, discussed above, have been described, for example XBBXBX (SEQ ID NO:13) and XBBBXXBX (SEQ ID NO:14) where B represents a basic residue (Hileman et al. Bioassays 1998, 20: 156-67). These segments have been shown by circular dichroism to form α-helices upon binding to GAGs (Verrecchio et al. J. Biol. Chem. 2000, 275(11): 7701-7707). If such sequences are placed for example in a concatameric or dendrimeric construct where for example three such sequences are presented—for example each as a ARRRAARA (SEQ ID NO:9) sequence—the resulting 24-mer peptide—for example ARRRAARA-ARRRAARA-ARRRAARA (SEQ ID NO:8)—ensures a retention in the extracellular matrix similar to high molecular weight polylysine, i.e. it is not washed out during a 4 hour perfusion period (Sakharov et al. FEBS Lett 2003, 27: 6-10).

Thus Growth factors and chemokines are naturally constructed with two types of binding motifs: one binding motif for the receptor through which signal transduction is achieved and one binding motif for GAG's through which attachment, and long-lasting local activity is achieved. Peptides such as PYY and NPY are neuropeptides and hormones, which are rather rapidly washed out of the tissue and are not optimized for long-lasting local activity. By attaching a GAG-binding motif to a Y2 selective agonist according to the present invention a bi-functional molecule similar to the growth factors and chemokines is constructed having both a receptor binding epitope in the PP-fold peptide part and a GAG-binding motif. An example of such an agonist is [Lys4,N-{(Ala-Arg-Arg-Arg-Ala-Ala-Ala-Arg-Ala)3; (SEQ ID NO:10)}-Lys13, Leu17,Ser30,Gln34] PP.

PEGylation

In PEGylation, a polyalkyleneoxide radical or radicals, is/are covalently coupled to peptidic or proteinaceous drugs to improve effective half life in the body following administration and to reduce immunogenicity, increase solubility etc. The term derives from the preferred polyalkyleneoxide used in such processes, namely that derived from ethylene glycol-polyethyleneglycol, or "PEG".

A suitable PEG radical may be attached to the agonist by any convenient chemistry, for example via a backbone amino acid residue of the agonist, and may also incorporate cleavable linkers (FEBS Lett. 2005 Apr. 25; 579(11):2439-44.). For instance, for a molecule like e.g. PEG, a frequently used attachment group is the epsilon-amino group of lysine or the N-terminal amino group. Other attachment groups include a free carboxylic acid group (e.g. that of the C-terminal amino acid residue or of an aspartic acid or glutamic acid residue), suitably activated carbonyl groups, mercapto groups (e.g. that of a cysteine residue), aromatic acid residues (e.g. Phe, Tyr, Trp), hydroxy groups (e.g. that of Ser, Thr or OH-Lys), guanidine (e.g. Arg), imidazole (e.g. His), and oxidized carbohydrate moieties.

When the agonist is PEGylated it usually comprises from 1 to 5 polyethylene glycol (PEG) molecules such as, e.g. 1, 2 or 3 PEG molecules. Each PEG molecule may have a molecular weight of from about 5 kDa (kiloDalton) to about 100 kDa, such as a molecular weight of from about 10 kDa to about 40 kDa, e.g., about 12 kDa or in another embodiment no more than about 20 kDa. In a particular embodiment of the invention, PEG 40 kDa is the PEGylating agent.

Suitable PEG molecules are available from Shearwater Polymers, Inc. and Enzon, Inc. and may be selected from SS-PEG, NPC-PEG, aldehyde-PEG, mPEG-SPA, mPEG-SCM, mPEG-BTC, SC-PEG, tresylated mPEG (U.S. Pat. No. 5,880,255), or oxycarbonyl-oxy-N-dicarboxyimide-PEG (U.S. Pat. No. 5,122,614).

Particular examples of PEGylated agonists of the invention are [Lys4,N-PEG5000-Lys13,Leu17,Ser30,Gln34]PP and [Lys4,N-PEG5000-Lys13,Leu17,Thr30,Gln34]PP.

Serum Albumin, GAG and PEG

Whether the modification to the agonist is attachment of a group to facilitate serum binding, GAG binding or improved stability via PEGylation, the serum albumin binding motif or GAG binding motif, or PEG radical may be, or may form part of, a side chain of a backbone carbon of the agonist corresponding to any of the following positions: 1, 3, 6, 7, 10, 11, 12, 13, 15, 16, 18, 19, 21, 22, 23, 25, 26, 28, 29, and 32.

Conjugation to Larger Biomolecules

The selective Y2 receptor agonists may be used as fusion proteins where they are linked for example to albumin or another protein or carrier molecule which provides beneficial pharmacokinetic or other types of properties such as for example decreased renal elimination. There are multiple chemical modifications and linkers which can be used for such a covalent attachment as known in the art, just as there are multiple proteins or carriers which can be used. Especially, covalent attachment of the selective Y2 peptide agonist to albumin is preferred, and at the positions in peptides which have been pointed out elsewhere herein in relation to modifications with the various motifs. In a preferred embodiment of the invention a peptide is fused to the C-terminal end of a large biomolecule such as albumin. Such fusion proteins can be produced through various semisynthetic techniques where the peptide may be made through peptide synthesis as described herein and the biomolecule through recombinant technology. The fusion protein may also be made entirely as a recombinant molecule expressed for example as a precursor molecule extended by a Gly-Lys-Arg sequence which when expressed as a secretory protein in eukaryotic cells will be cleaved by biosynthetic enzymes and the Gly turned into the carboxyamide on the C.terminal Tyr residue of the C-terminal Y2 receptor recognition sequence.

Helix Inducing Peptides

Acylation of the N-terminus of the agonists with which the invention is concerned has been mentioned as a means of stabilising the agonist against the action of aminopeptidases. Another stabilising modification involves the covalent attachment of a stabilizing peptide sequence of 4-20 amino acid residues covalently at the N- and/or the C-terminus, preferably the N-terminus. The amino acid residues in such a peptide are selected from the group consisting of Ala, Leu, Ser, Thr, Tyr, Asn, Gln, Asp, Glu, Lys, Arg, His, Met and the like. In an interesting embodiment the N-terminal peptide attachment comprises 4, 5 or 6 Lys residues, for example Lys-Lys-Lys-Lys-Lys-Lys-[Lys4,Leu17,Ser30,Gln34]PP (SEQ ID NO:11). These can be linked at the N-terminus of the peptide agonist. A general description of such stabilizing peptide extensions is given in WO 99/46283 (Zealand Pharmaceuticals), which is hereby incorporated by reference.

The receptor agonists with which the invention is concerned may be prepared by well-known methods such as, e.g., a synthetic, semisynthetic and/or recombinant method. The methods include standard peptide preparation techniques such as, e.g., solution synthesis, and solid-phase synthesis. Based on textbook and general knowledge within the field, a person skilled in the art knows how to proceed in order to obtain the agonists and derivatives or modifications thereof.

Clinical Indications

The Y2-specific agonists with which the invention is concerned are of value in the treatment of conditions responsive to activation of Y2 receptors. Such conditions include those for which regulation of energy intake or energy metabolism, or induction of angiogenesis, is indicated. For any such use, the agonist may be one which comprises a modification or motif which confers stability towards peptidases, serum protein binding properties, or PEGylation to prolong serum and/or tissue half-life. Especially for induction of angiogenesis, the agonist may comprise a GAG-binding motif to prolong tissue half-life and Y receptor exposure.

Diseases or conditions where induction of angiogenesis is indicated include peripheral vascular disease, coronary vascular disease, myocardial infarction, stroke, conditions in which any of the foregoing is considered a contributory factor, wound healing and tissue repair.

Diseases or conditions in which regulation of energy intake or energy metabolism is indicated include obesity and overweight, and conditions in which obesity and overweight are considered contributory factors, such as bulimia, bulimia nervosa, Syndrome X (metabolic syndrome), diabetes, type 2 diabetes mellitus or Non Insulin Dependent Diabetes Mellitus (NIDDM), hyperglycemia, insulin resistance, impaired glucose tolerance, cardiovascular disease, hypertension, atherosclerosis, coronary artery disease, myocardial infarction, peripheral vascular disease. stroke, thromboembolic diseases, hypercholesterolemia, hyperlipidemia, gallbladder disease, osteoarthritis, sleep apnea, reproductive disorders such as polycystic ovarian syndrome, or cancer of the breast, prostate, or colon.

1. Obesity and Overweight

PYY3-36 has been shown to decrease appetite, food intake and body weight in various rodents (Batterham et al. *Nature* 2002, 418: 595-7; Challis et al. *BBRC* Nov. 2003, 311: 915-9) as well as to decrease appetite and food intake in man (Batterham et al 2002). The animal data including studies in receptor knock out animals strongly indicate that this effect of PYY3-36 is mediated through Y2 receptors and through NPY/AgRP and POMC neurones in the arcuate nucleus. Interestingly, the effect is very long lasting and is seen up to 24 hours after for example a single intra-peritoneal injection of PYY3-36. Such long lasting effects on appetite etc, is well know also from ICV injection of especially AgRP. PYY levels and the PYY food responses are lower in obese subjects and correlates inversely with their BMI. Importantly, obese subject are not resistant to the effect of PYY as infusion of PYY3-36 for 90 minutes decreases food intake in obese subjects in a similar long lasting fashion (Batterham et al. 2003, *NEJM* 349: 941-48).

Hence, the Y2 selective agonists with which the invention is concerned are suitable for use in a subject, such as a mammal including a human, in order to regulate the energy intake. Accordingly, the invention relates to methods for altering energy intake, food intake, appetite, and energy expenditure. A method is disclosed herein for reducing energy or food intake by administering to a subject a cosmetically or therapeutically effective amount of the agonist of the invention In a further embodiment, a method is disclosed herein for altering energy metabolism in a subject. The method includes administering a therapeutically effective amount of an agonist of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat. In a further embodiment a method is disclosed herein for any and all manipulations of the arcuate circuitry described in this application, that alter food intake coordinately and reciprocally alter energy expenditure. Energy expenditure is a result of cellular metabolism, protein synthesis, metabolic rate, and calorie utilization. Thus, in this embodiment, peripheral administration results in increased energy expenditure, and decreased efficiency of calorie utilization. In one embodiment, a therapeutically effective amount of a receptor agonist according to the invention is administered to a subject, thereby increasing energy expenditure.

In several embodiments both relating to the therapeutic use and to the cosmetic use, the Y2 selective agonist can be used for weight control and treatment, reduction or prevention of obesity, in particular any one or more of the following: preventing and reducing weight gain; inducing and promoting weight loss; and reducing obesity as measured by the Body Mass Index. As mentioned above, the invention also relates to the use of the Y2 selective agonist for controlling any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. The disclosure further relates to the use of the Y2 selective agonist in maintaining any one or more of a desired body weight, a desired Body Mass Index, a desired appearance and good health.

In a further or alternative aspect, the invention relates to a method for the treatment and/or prevention of reduced energy metabolism, feeding disorders, appetite disorders, overweight, obesity, bulimia, bulimia nervosa, Syndrome X (metabolic syndrome), or complications or risks associated thereto including diabetes, type 2 diabetes mellitus or Non Insulin Dependent Diabetes Mellitus (NIDDM), hyperglycemia, insulin resistance, impaired glucose tolerance, cardiovascular disease, hypertension, atherosclerosis, congestive heart failure, stroke, myocardial infarct, thromboembolic diseases, hypercholesterolemia, hyperlipidemia, gallbladder disease, osteoarthritis, sleep apnea, reproductive disorders such as polycystic ovarian syndrome, cancers of the breast, prostate, and colon, the method comprising administering to a subject such as a mammal including a human, an effective dose of one or more of the Y2 selective agonists as described herein.

2. Therapeutic Angiogenesis

A number of in vitro studies on effects on growth of vascular smooth muscle cells, hyperthrophy of ventricular cardiomyocytes as well as endothelial cell proliferation and migration have suggested that NPY may act as an angiogenic factor (Zukowska-Grojec et al. 1998 *Circ. Res.* 83: 187-95). Importantly, in vivo studies using both the mouse corneal micropocket model as well as the chick chorioallantoic membrane (CAM) assay has confirmed that NPY is a potent angiogenic factor which gives rise to vascular tree-like structures showing vasodilation as observed otherwise only with fibroblast growth factor-2 (FGF-2) and not for example vascular endothelial growth factor (VEGF) angiogenic structures (Ekstrand et al. 2003 *PNAS* 100: 6033-38). In the developing chick embryo NPY induced vascular sprouting from preexisting blood vessels. The effect of NPY was not observed in Y2 receptor knock out animals indicating that the Y2 receptor is responsible for the angiogenic effect of NPY (Ekstrand et al 2003). This notion is also supported by observations that the Y2 receptor is highly upregulated in ischemic vessels and the enzyme which generates the endogenous, selective Y2 ligand PYY3-36, dipentidylpeptidase-IV is also highly upregulated.

In various cardiovascular diseases such as atherosclerosis, for example, it is contemplated that induction of angiogenesis would be beneficial in peripheral vessels as well as in coronary vessels. Also induction of angiogenesis is believed to be beneficial for securing reperfusion after myocardial infarction. FGF-2 has been proposed to be an especially efficient agent for induction of angiogenesis in patients with cardiovascular diseases. However, like most other angiogenic factors FGF-2 is a growth factor and has the potential of stimulating tumor growth also by providing angiogenesis. As presented above, NPY acting through Y2 receptors induces neovascularization of a similar type as induced by FGF-2. However NPY is a neuropeptide and not a classical growth factor and has not been implicated in inducing tumor growth. Thus, a Y2 agonist is a useful agent for therapeutic angiogenesis. However, it is particularly important for this use that the agonist does not show Y1 receptor agonism because this will give unwanted cardiovascular effects. This means that all the peptides with which the invention is concerned are Y2 selective receptor agonists and are especially useful therapeutic agents also with respect of inducing angiogenesis. They are particularly useful when modified with GAG binding motifs, as discussed above. To elaborate further: The action of FGF-2, as that of most other classical growth factors, is partly mediated or controlled through binding to glycosaminoglycans (GAG) in the extracellular matrix. This binding to GAGs ensures that the angiogenic factor acts in an appropriate spatial and temporal fashion and that it is not washed out of the tissue rapidly. For the use of small peptides and peptide mimics in therapeutic angiogenesis, such as the ones described in the present invention, this is particularly important. In one embodiment of the invention the peptides incorporate one or more GAG binding motifs, which ensures that they attach to GAGs in the extracellular matrix to induce optimal angiogenesis after administration. This can, for example, be by intravenous or intraarterial administration or, for example, direct administration into the coronary arteries in order to induce cardiac angiogenesis during coronary artery disease and/or post acute myocardial infarction. Similarly such a compound can be administered through intraarterial injection in the femoral artery for treatment of peripheral vascular disease. It can also be, for example, by topical local administration to skin lesions in order to promote improved wound healing. A prolonged Y receptor exposure efficient in inducing angiogenesis can also be obtained by using a peptide according to the present invention modified with a serum albumin binding motif.

One embodiment of the invention the Y2 selective agonists comprise a GAG-binding motif, which is placed in a position where it does not impair the stability of the peptide or impair the potency and selectivity of the peptide.

Accordingly, in one embodiment the invention relates to the use the Y2 selective receptor agonist for modifying disturbances in the angiogenesis system, especially for inducing angiogenesis such as angiogenesis associated with diseases or conditions such as e.g., cardiovascular diseases including peripheral vascular disease with symptoms such as cladicatio intermittens, coronary artery disease and myocardial infarction; tissue repair processes including wound healing in the skin, inflammatory conditions including inflammatory conditions in the gastrointestinal tract such as, e.g., ulcers, colitis, inflammatory bowel disease, Crohns disease etc.

A specific embodiment is to use the receptor agonist for inducing angiogenesis in a heart or in a blood vessel, or in a tissue such as a mucosal tissue including the gastro-intestinal mucosa and the skin.

3. Wound Healing

In animals where the Y2 receptor has been selectively eliminated through the deletion of its gene it has been reported that wound healing is impaired and that the associated neo-vascularization is impaired (Ekstrand et al. 2003 *PNAS* 100: 6033-38). Thus the selective Y2 agonists of the present invention are useful to improve wound healing. The peptides can for this indication be administered in various way including parenteral administration. However, a preferred route of administration is topical application e.g. in the form of a solution, dispersion, powders, sticks, creme, ointment, lotion, gel, hydrogel, transdermal delivery system including patches and plasters, etc. For topical administration they can be used as such. However, in a preferred embodiment of the invention, the peptides have been modified with one or more of the GAG-binding motifs described herein to ensure a long lasting, local effect of the peptide through binding to GAGs in the tissue.

4. Inflammatory Bowel Disease

PYY has previously been described for the prevention and/or treatment of inflammatory bowel disease; see WO 03/105763 to Amylin Pharmaceuticals, Inc, which is hereby incorporated by reference. Therefore the agonists with which the invention is concerned are effective in the treatment or prevention of inflammatory bowel disease as well. Accordingly, the present invention also relates to the use of the agonists described herein for such medical use. In an interesting embodiment, the peptides comprise one or more GAG-binding motifs, cf. above.

5. Osteoporosis

Several studies in Y2 knock out animals have shown very strong effects on trabecular bone formation (eg Sainsbury et al. *Mol. Cell. Biol.* 2003, 23: 5225-33). Y2 receptor is also involved in bone formation, cf. Baldock et al. 2002 J. Clin. Invest 109: 915-21. Thus the present Y2-selective agonists are useful for the treatment of osteoporosis. Especially, it is contemplated that the peptides comprising one or more GAG-binding motifs are suitable for use in osteoporosis or related diseases.

In a subgroup of the population, Y2 agonists may not have the intended action due to genetic variations such as polymorphisms in the Y2 gene. Loss of function mutations in these receptors are likely to be associated with obesity. Thus, in a preferred embodiment of the invention an analysis of the Y2 gene of the subject to be treated is performed in order to probe for polymorphisms/mutations in these genes and identification of such polymorphisms. Based on such an analysis an optimal treatment of the subjects can be made. For example, only subjects with normal genotype or with polymorphisms, which do not affect the function of Y2 agonists, should be treated with such agonists. Another possibility is to increase the dose of the Y2 agonist in subjects who express an impaired receptor in order to ensure an optimal effect of the drug. In the case where the obesity of a subject is caused by an impairment in the function of the Y2 receptor it could be argued that treatment with a—for example large doses—of the Y2 agonist is a form of replacement therapy—provided that at least some of the relevant receptor function is still left—for example in heterozygote patients.

In one embodiment of the invention an acute test may be performed where the Y2 agonist is administered to ensure that these compounds have the intended effect in the subject to be treated before a chronic treatment is started. Through these means it is ensured that only subjects who are susceptible to treatment with Y2 agonists are treated with these compounds.

Dosages

The therapeutically effective amount of a Y2 receptor agonist according to the invention will be dependent on specific agonist employed, the age, weight and condition of subject being treated, the severity and type of the condition or disease being treated, the manner of administration and the strength of the composition applied.

For example, a therapeutically effective amount of the Y2 receptor agonist thereof can vary from about 0.01 μg per kilogram (kg) body weight to about 1 g per kg body weight, such as about 1 μg to about 5 mg per kg body weight, or about 5 μg to about 1 mg per kg body weight. In another embodiment, the receptor agonist is administered to a subject at 0.5 to 135 picomole (pmol) per kg body weight, or about 72 pmol per kg body weight.

In one specific, non-limiting example from about 5 to about 50 nmol is administered as a subcutaneous injection, such as from about 2 to about 20 nmol, or about 1.0 nmol is administered as a subcutaneous injection. The exact dose is readily determined by one skilled in the art based on the potency of the specific compound (such as the receptor agonist) utilized, the age, weight, sex and physiological condition of the subject.

The amounts can be divided into one or several doses for administration daily, every second day, weekly, every two weeks, monthly or with any other suitable frequency. Normally, the administration is once or twice daily.

Methods of Administration

The Y2 receptor agonist as well as cosmetic or pharmaceutical compositions according to the invention can be administered by any route, including the enteral (e.g. oral administration) or parenteral route. In a specific embodiment, the parenteral route is preferred and includes intravenous, intraarticular, intraperitoneal, subcutaneous, intramuscular, intrasternal injection and infusion as well as administration by the sublingual, transdermal, topical, transmucosal including nasal route, or by inhalation such as, e.g., pulmonary inhalation. In specific embodiments, the subcutaneous and/or the nasal administration route is preferred.

The receptor agonists can be administered as such dispersed in a suitable vehicle or they can be administered in the form of a suitable pharmaceutical or cosmetic composition. Such compositions are also within the scope of the invention. In the following are described suitable pharmaceutical compositions. A person skilled in the art will know how that such composition may also be suitable for cosmetic use or he will know how to adjust the compositions to cosmetic compositions by use of suitable cosmetically acceptable excipients.

Pharmaceutical Compositions

The receptor agonists (also denoted "compounds") according to the invention for use in medicine or cosmetics are normally presented in the form of a pharmaceutical composition comprising the specific compound or a derivative thereof together with one or more physiologically or pharmaceutically acceptable excipients.

The compounds may be administered to an animal including a mammal such as, e.g., a human by any convenient administration route such as, e.g., the oral, buccal, nasal, ocular, pulmonary, topical, transdermal, vaginal, rectal, ocular, parenteral (including inter alia subcutaneous, intramuscular, and intravenous cf. above), route in a dose that is effective for the individual purposes. A person skilled in the art will know how to chose a suitable administration route. As mentioned above, the parenteral administration route is preferred. In a specific embodiment, the receptor agonists are administered subcutaneously and/or nasally. It is well known in the art that subcutaneous injections can be easily self-administered.

A composition suitable for a specific administration route is easily determined by a medical practitioner for each patient individually. Various pharmaceutically acceptable carriers and their formulation are described in standard formulation treatises, e.g., Remington's Pharmaceutical Sciences by E. W. Martin.

The pharmaceutical composition comprising a compound according to the invention may be in the form of a solid, semi-solid or fluid composition. For parenteral use, the composition is normally in the form of a fluid composition or in the form of a semi-solid or solid form for implantation.

Fluid compositions, which are sterile solutions or dispersions can utilized by for example intravenous, intramuscular, intrathecal, epidural, intraperitoneal or subcutaneous injection of infusion. The compounds may also be prepared as a sterile solid composition, which may be dissolved or dispersed before or at the time of administration using e.g. sterile water, saline or other appropriate sterile injectable medium.

The fluid form of the composition may be a solution, an emulsion including nano-emulsions, a suspension, a dispersion, a liposomal composition, a mixture, a spray, or a aerosol (the two latter types are especially relevant for nasal administration).

Suitable mediums for solutions or dispersions are normally based on water or pharmaceutically acceptable solvents e.g. like an oil (e.g. sesame or peanut oil) or an organic solvent like e.g. propanol or isopropanol. A composition according to the invention may comprise further pharmaceutically acceptable excipients such as, e.g., pH adjusting agents, osmotically active agents e.g. in order to adjust the isotonicity of the composition to physiologically acceptable levels, viscosity adjusting agents, suspending agents, emulsifiers, stabilizers, preservatives, antioxidants etc. A preferred medium is water.

Compositions for nasal administration may also contain suitable non-irritating vehicles such as, e.g., polyethylene glycols, glycofurol, etc. as well as absorption enhancers well known by a person skilled in the art (e.g. with reference to Remington's Pharmaceutical Science)

For parenteral administration, in one embodiment the receptor agonists can be formulated generally by mixing it at the desired degree of purity, in a unit dosage injectable form (solution, suspension, or emulsion), with a pharmaceutically acceptable excipient or carrier, i.e., one that is non-toxic to recipients at the dosages and concentrations employed and is compatible with other ingredients of the composition.

Generally, the formulations are prepared by contacting the receptor agonist uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Due to the amphiphatic nature of the peptides described herein suitable forms also include micellar formulations, liposomes and other types of formulations comprising one or more suitable lipids such as, e.g., phospholipids and the like.

Preferably, they are suspended in an aqueous carrier, for example, in an isotonic buffer solution at a pH of about 3.0 to about 8.0, preferably at a pH of about 3.5 to about 7.4, 3.5 to 6.0, or 3.5 to about 5. Useful buffer substances include acetate, citrate, phosphate, borate, carbonate such as, e.g., sodium citrate-citric acid and sodium phosphate-phosphoric acid, and sodium acetate/acetic acid buffers.

The compositions may also be designed to controlled or prolonged delivery of the receptor agonist after administration in order to obtain a less frequent administration regimen. Normally a dosage regimen including 1-2 daily administrations is considered suitable, but within the scope of the present invention is also included other administration regimens such as, e.g., more frequent and less frequent. In order to achieve a prolonged delivery of the receptor agonist, a suitable vehicle including e.g. lipids or oils may be employed in order to form a depot at the administration site from which the receptor agonist is slowly released into the circulatory system, or an implant may be used. Suitable compositions in this respect include liposomes and biodegradable particles into which the receptor agonist has been incorporated.

In those situations where solid compositions are required, the solid composition may be in the form of tablets such as, e.g. conventional tablets, effervescent tablets, coated tablets, melt tablets or sublingual tablets, pellets, powders, granules, granulates, particulate material, solid dispersions or solid solutions.

A semi-solid form of the composition may be a chewing gum, an ointment, a cream, a liniment, a paste, a gel or a hydrogel.

Other suitable dosages forms of the pharmaceutical compositions according to the invention may be vagitories, suppositories, plasters, patches, tablets, capsules, sachets, troches, devices etc.

The dosage form may be designed to release the compound freely or in a controlled manner e.g. with respect to tablets by suitable coatings.

The pharmaceutical composition may comprise a therapeutically effective amount of a compound according to the invention.

The content of a compound of the invention in a pharmaceutical composition of the invention is e.g. from about 0.1 to about 100% w/w of the pharmaceutical composition.

The pharmaceutical compositions may be prepared by any of the method well known to a person skilled in pharmaceutical formulation.

In pharmaceutical compositions, the compounds are normally combined with a pharmaceutical excipient, i.e. a therapeutically inert substance or carrier.

The carrier may take a wide variety of forms depending on the desired dosage form and administration route.

The pharmaceutically acceptable excipients may be e.g. fillers, binders, disintegrants, diluents, glidants, solvents, emulsifying agents, suspending agents, stabilizers, enhancers, flavours, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook.

The following examples describe the preparation and activities of some specific agonists of the invention.

Syntheses

The peptides were synthesized with an Applied Biosystem Inc. (ABI) Model 433 automated synthesizer based on the solid phase peptide synthesis (SPPS) approach using Fmoc chemistry. All the reagents for the ABI synthesizer were purchased from ABI (except piperidine was from Aldrich). Fmoc amino acids were purchased from ABI. Rink Amide MBHA resins were from Novabiochem. Standard 0.25 mmole Fast-Moc chemistry was used. The general Fmoc chemistry protocol for SPPS includes: 1) cleavage of the Fmoc protection groups with 20% piperidine; 2) activation of the carboxyl group of amino acids; and 3) coupling of the activated amino acids to the amino-terminal of the resin bound peptide chain to form peptide bonds. Amino acids were activated with 2-(1H-benzotriazol-1-yl)-1,1,3,3-tetramethyluronium hexafluorophosphate (HBTU). 1.0 mmole of dry protected amino acid in a cartridge was dissolved in a solution of HBTU, N,N-diisopropylethylamine (DIEA), and 1-hydroxybenzotriazole (HOBt) in N,N-dimethylformamide (DMF) with additional N-methylpyrrolidinone (NMP) added. The activated Fmoc amino acid was formed almost instantaneously and the solution was transferred directly to the reaction vessel. The step of Fmoc deprotection was monitored and controlled by conductivity measurement. The final synthesis was product was washed extensively with NMP and dichloromethane (DCM).

Deprotection: The resins containing synthesized peptides were unloaded from the synthesizer and briefly air-dried. Using 5-10 ml of the cleavage cocktail (95% trifluoroacetic acid (TFA), 2.5% triisopropylsilane (TIS) in water) for 4.0 hours at room temperature, the peptides were cleaved off the resin and at the same time, the side chain protection groups [O-t-butyl (OtBu) for Asp, Glu, Tyr, Thr and Ser; Pentamethylchroman-6-sulfonyl (Pmc) for Arg, t-butoxycarbonyl (Boc) for Lys; trityl (Trt) for Asn and Gln, were removed under the deprotection conditions. The peptide solution was separated from the resin by filtration and precipitated in 40 ml of cold diethyl ether. The peptide was recovered by centrifugation and washed 2×40 ml of cold diethyl ether. The peptide was lyophilized and stored at −20° C. before purification.

Purification and Characterization: The peptide powder was dissolved in 50% acetic acid solution and injected onto a semi-preparative reverse phase HPLC column for purification. A HPLC system with dual wavelength (220 nm and 280 nm) uv detector was used. A linear gradient of acetonitrile was programmed and introduced to the column to separate the peptide product from other substances. The eluant was collected by a fraction collector, and the individual separation fractions were subjected to both analytical HPLC and MALDI-TOF MS for characterization to ensure identity and purity.

Example 1

Synthesis of Lys4,Leu17,Thr30,Gln34]hPP (SEQ ID No: 5); [M+H]$^+$: 4162.2

Based on the 0.70 mmole/g substitution rate for the Rink Amide MBHA resin (Novabiochem), 0.357 g of the resin was weighed out for 0.25 mmole scale synthesis. The performance of the PE-ABD 433 peptide synthesizer was checked before the run with various flow tests to ensure accurate reagent delivery. Fmoc amino acids: Asp-OtBu, Tyr-OtBu, Thr-OtBu, Arg-Pmc, Trp-Boc, Lys-Boc, Glu-OtBu, Asn-Trt, Gln-Trt, Val, Leu, Ile, Ala, Pro, and Gly were purchased commercially in 1 mmole cartridges. Other synthesis reagents and solvents were purchased commercially and loaded onto the instrument according to the instrument's instruction. A chemistry program called 0.25 mmole Mon-PrePk was used for synthesizing this peptide. Double coupling was performed for the first four N-terminal amino acids (Ala-Pro-Leu-Lys) to enhance the synthesis efficiency. The Fmoc deprotection was monitored and controlled by conductivity measurement with set criteria of 5% or less conductivity compared to the previous deprotection cycle. The overall synthesis yield for this series of peptides (linear) was better than 60%, as determined by analytical HPLC.

The resin was air-dried and transferred into a glass vial and 10 ml of freshly prepared cleavage reagent (95% trifluoroacetic acid (TFA), 2.5% triisopropylsilane (TIS) in water) was added. The deprotection reaction was carried out for 4 hours at room temperature with constant stirring. The supernatant was then separated from the resin by filtration. The peptide was precipitated with 40 ml of ice-cold diethyl ether followed by centrifugation (6 min at 3,500×rpm) for recovery. The precipitated peptide was washed twice with cold diethyl ether. The peptide solution was freeze-dried overnight.

The peptide was re-dissolved in 50% acetic acid and purified on a Vydac C8 reverse phase HPLC column (1.0 cm I.D., 25 cm length with 5 µm particle size, and 300 Å pore size) using a linear gradient of 0-70% solvent B with solvent A in 70 min at a flow rate 3 ml/min. The composition of solvents A and B were as follows: A: 0.1% TFA, 2% acetonitrile in water; B: 0.1% TFA in 95% aqueous acetonitrile. The fractions were collected at every 0.1 min. Aliquots of each fraction were analyzed by both MS and analytical RP-HPLC. The fractions that contained a single u.v. 220 nm absorbance peak with the expected mass unit for the peptide ([M+H]$^+$: 4162.2) were combined and lyophilized. The final purity (95%) of the peptide was determined by RP-HPLC analysis of the combined fractions.

The peptide listed below was synthesized according to the same protocol as Example 1, but with the modifications noted.

Example 2

Synthesis of [Lys4,Leu17,Ser30,Gln34]hPP (SEQ ID No: 4) [M+H]$^+$: 4148.2

Prepared according to Example 1, with the exception that Fmoc-Ser-OtBu was used instead of Fmoc-Thr-OtBu.

Example 3

Synthesis of [Lys4,Leu17, Met-sulfoxide30,Gln34]hPP (SEQ ID No: 6) [M+H]: 4207.2

[Lys4, Leu17, Met30, Gln34]hPP was prepared according to Example 1, with the exception that Fmoc-Met was used instead of Fmoc-Thr-OtBu. The purified [Lys4, Leu17, Met30, Gln34]hPP peptide was then oxidized in 0.14% hydrogen peroxide to yield [Lys4, Leu17, Met-sulfoxide30, Gln34]hPP: 0.65 mg of [Lys4, Leu17, Met30, Gln34]hPP was dissolved in 1.5 ml of phosphate buffer. 75 µl of 3% hydrogen peroxide was then added to the peptide solution. The oxidation reaction was carried out for 12 hours in the dark. An aliquot of the peptide was analyzed by both analytical reverse phase HPLC and MALDI-TOF MS. The shift of [M+H] from 4191.2 ([Lys4, Leu17, Met30, Gln34]hPP) to 4207.2 indicated oxidation of Met to Met-sulfoxide at the 30 position ([Lys4, Leu17, Met-sulfoxide30, Gln34]hPP). The parent unoxidized peptide was no more than 4% based on uv detection at 220 nm.

Biological Assays and Results

I. In Vitro Assays to Determine Peptide Affinity and Potency

Cloning and Expression of the Rhesus Monkey Y Receptors

The coding region of the rhesus monkey NPY-Receptors (Y1, Y2, Y4) were sub-cloned into the pcDNA3.1/Zeo vector containing HA-signal sequence-Flag Tag on the amino terminus as described in X.-M. Guan et. al. J. Biol. Chem. 267(31):21995-21998 (1992), and used for expression, binding, and functional studies to identify Y2-selective peptides. The rhY1 is identical to Genbank sequence AF303089. The rhY2 is identical to Genbank sequence AF303090. The rhY4 is identical to Genbank sequence AY149475.1.

Rhesus Monkey Y2 Receptor Affinity Assay

Affinity of test compounds for the rhesus monkey Y2 receptor is determined in a competition binding assay using human 125I-PYY binding in CHO cells stably transfected with the rhesus monkey Y2 receptor.

The stable transfected CHO cells are transferred to 48-well culture plates one day prior assay at a density of 2,500 cells per well aiming at 5-8% binding of the radioactive ligand. The following day, competition binding experiments are performed for 3 hours at 4 C.° using 12 pM of human 125I-PYY (Amersham, Little Chalfont, UK). Binding assays are performed in 0.5 ml of a 50 mM Hepes buffer, pH 7.4, supplemented with 1 mM CaCl2, 5 mM MgCl2, and 0.1% (w/v) bovine serum albumin and 100 µg/ml bacitracin. Non-specific binding is determined as the binding in the presence of 1 µM of unlabeled human PYY. Cells are washed twice in 0.5 ml of ice-cold buffer and 0.5-1 ml of lysis buffer (8 M Urea, 2% NP40 in 3 M acetic acid) is added and the bound radioactivity is counted in a gamma counter. Determinations are made in triplicates. Steady state binding is reached with the radioactive ligand under these conditions. IC50 values were calculated using a standard pharmacological data handling software, Prism 3.0 (graphpad Sofware, San Diego, USA). Ki-values are calculated according the Cheng-Prusoff equation (Cheng Y, Prusoff W H., Biochem Pharmacol. 1973): Ki=[IC50/(1+[L]/Kd)], where Ki is the equilibrium inhibitory constant for the cold ligand, Kd is the equilibrium constant for the radiolabeled (hot) ligand and L is the concentration of the radiolabeled ligand used.

Rhesus Monkey Y4 Receptor Affinity Assay

Protocol as for the Y2 affinity assay, except that CHO cells stably expressing rhesus monkey Y4 are used and cells are transferred to culture plates at a density of 125,000 cells per well. The competition assay uses human 125I-PP, and human PP is used for the determination of non-specific binding.

Rhesus Monkey Y1 Receptor Affinity Assay

Protocol as for the Y2 affinity assay, except that CHO cells stably expressing rhesus monkey Y1 are used and cells are transferred to culture plates at a density of 23,000 cells per well. The competition assay uses human 125I-PYY, and human PYY is used for the determination of non-specific binding.

The results of testing NPY, PYY. PYY3-36, PP and the agonists of the invention at the Y2 receptors in the above affinity assay is given in Table 1.

TABLE 1

| Compound | | Competition binding w $^{126}$I-PYY at Y2 (Ki, nM) |
|---|---|---|
| SEQ ID No: 2 | PYY | 0.09 (8) |
| SEQ ID No: 1 | NPY | 0.11 (1) |
| | PYY3-36 | 0.32 (3) |
| SEQ ID No: 3 | PP | >1000 |
| SEQ ID No: 4 | [Lys4, Leu17, Ser30, Gln34]-PP | 0.51 (2) |
| SEQ ID No: 5 | [Lys4, Leu17, Thr30, Gln34]-PP | 0.47 (4) |
| SEQ ID No: 6 | [Lys4, Leu17, Met(O)30, Gln34]-PP | 0.06 (1) |

Values in parentheses shows number of independent experiments.

In the above affinity assay, the peptides represented by SEQ ID Nos. 4-6 are ≧100-fold selective against the Y1 receptor and ≧20-fold selective against the Y4 receptor.

Rhesus Monkey Y2 Receptor Potency Assay

Potency of the test compounds on the rhesus monkey Y2 receptor is determined by performing dose-response experiments in COS-7 cells transiently transfected with the rhesus monkey Y2 receptor as well as a chimeric G protein, Gqi5 which ensures that the Y2 receptor couples through a Gq pathway leading to an increase in inositol phosphate turnover.

Phosphatidylinositol turnover—One day after transfection COS-7 cells are transferred to 96-wells culture plates at a density of 30,000 cells per well and incubated for 24 hours with 0.5 μCi of [3H]-myo-inositol (Amersham, PT6-271) in 100 μl medium supplemented with 10% fetal calf serum, 2 mM glutamine and 0.01 mg/ml gentamicin per well. Cells are washed twice in buffer, 20 mM HEPES, pH 7.4, supplemented with 140 mM NaCl, 5 mM KCl, 1 mM MgSO4, 1 mM CaCl2, 10 mM glucose, 0.05% (w/v) bovine serum; and are incubated in 100 μl buffer supplemented with 10 mM LiCl at 37° C. for 30 min. After stimulation with various concentrations of peptide for 45 min at 37° C., cells are extracted with 50 μl 10% ice-cold perchloric acid followed by incubation on ice for 30 min. 20 μl of the perchloric acid cell solution is transferred into a solid white 96 wells plate. 80 μl of SPA YSI beads (12.5 mg/ml) (=1 mg/well) is added, the plate are sealed and shaked up to 30 minutes. Following the plate is centrifuged for 5 min at 1500 rpm and read in Packard Topcounter. Determinations are made in duplicates. EC50 values were calculated using a standard pharmacological data handling software, Prism 3.0 (graphPad Sofware, San Diego, USA).

Rhesus Monkey Y4 Receptor Potency Assay

Protocol as for the Y2 potency assay, except that rhesus monkey Y4-transformed COS-7 cells are used.

Rhesus Monkey Y1 Receptor Potency Assay

Protocol as for the Y2 potency assay, except that rhesus monkey Y1-transformed COS-7 cells are used.

The results of testing NPY, PYY, PYY3-36, PP and the agonists of the invention at

TABLE 2

| Compound | | IP3 EC50 values at Y2 (nM) |
|---|---|---|
| SEQ ID No: 2 | PYY | 0.18 (9) |
| SEQ ID No: 1 | NPY | 0.60 (4) |
| SEQ ID No: 3 | PP | >1 μM (2) |
| | PYY3-36 | 0.29 (9) |
| SEQ ID No: 3 | [Lys4, Leu17, Ser30, Gln34]-PP | 0.67 (3) |
| SEQ ID No: 4 | [Lys4, Leu17, Thr30, Gln34]-PP | 0.71 (4) |
| SEQ ID No: 5 | [Lys4, Leu17, Met(O)30, Gln34]-PP | 0.50 (2) |

Values in parentheses shows number of independent experiments.

In the above potency assay, the peptides represented by SEQ ID Nos. 4-6 are ≧100-fold selective against the Y1 receptor and ≧20-fold selective against the Y4 receptor.

II. In Vitro Assay to Determine Binding to Glycosamino Glycans (GAGs)

The ability of test compounds to bind to GAGs is monitored in an in vitro assay using immobilized heparin, i.e. for example either a HiTrap heparin-Sepharose column (Amersham Pharmacia Biotech, Uppsala, Sweden) or a heparin HPLC columns which are eluted with a 50-min linear gradient of 0-0.5 M NaCl in 50 mM sodium phosphate (pH 7.3) containing 2 mM DTT and 1 mM MgEDTA at a flow rate of 1 ml/min. For regeneration, the column was washed with 1 M NaCl in buffer A from 51-55 min. For initial analytical purposes a step-gradient of NaCl can be used.

The invention claimed is:

1. A peptide selected from the group consisting of
   (i) [Lys4,Leu17,Ser30,Gln34]hPP (SEQ ID NO:4),
   (ii) [Lys4,Leu17,Thr30,Gln34]hPP (SEQ ID NO:5);
   (iii) [Lys4,Leu17,oxidised Met30,Gln34]hPP (SEQ ID NO:6); and
   (iv) analogues of (i), (ii) or (iii) which are
      (a) conservatively substituted in one or more positions other than positions 4, 17, 30 and 34 and/or
      (b) N-terminally acylated, PEGylated, or covalently coupled to a serum albumin binding motif, a glycosaminoglycan binding motif or a helix inducing motif said covalent coupling being to a residue of peptide (i), (ii) or (iii) or to a residue substituted in peptide (i), (ii) or (iii) which provides a functional group for such covalent binding.

2. A peptide as claimed in claim 1 wherein the oxidised Met30 is a sulfoxide.

3. A peptide as claimed in claim 1 which is acylated at its N-terminus.

4. A peptide as claimed in claim 3 which is acylated at its N-terminus with a carbon chain having from 2 to 24 carbon atoms.

5. A peptide as claimed in claim 3 which is acetylated at its N-terminus.

6. A peptide as claimed in claim 1 which comprises a serum albumin binding motif, or a glycosaminoglycan (GAG) binding motif, or a helix inducing motif, or is PEGylated.

7. A peptide as claimed in claim 6 comprising a serum albumin binding motif, wherein the serum albumin binding motif is a lipophilic group.

8. A peptide as claimed in claim 7 wherein the lipophilic group comprises an optionally substituted, saturated or unsaturated, straight or branched hydrocarbon group of from 10 to 24 carbon atoms.

9. A peptide as claimed in claim 7 which comprises a side chain to the backbone of the peptide, wherein the side chain comprises the lipophilic group.

10. A peptide as claimed in claim 9 wherein the side chain is connected to a residue in the backbone via an ether, thioether, amino, ester or amide bond.

11. A peptide as claimed in claim 10 wherein the side chain is selected from the group consisting of:
   $CH_3(CH_2)_nCH(COOH)NH\text{—}CO(CH_2)_2CONH\text{—}$, wherein n is an integer from 9 to 15,
   $CH_3(CH_2)_rCO\text{—}NHCH(COOH)(CH_2)_2CONH\text{—}$, wherein r is an integer form 9 to 15, and
   $CH_3(CH_2)_sCO\text{—}NHCH((CH_2)_2COOH)CONH\text{—}$, wherein s is an integer from 9 to 15,
   $CH_3(CH_2)_mCONH\text{—}$, wherein m is an integer from 8 to 18,
   $\text{—}NHCOCH((CH_2)_2COOH)NH\text{—}CO(CH_2)_pCH_3$, wherein p is an integer from 10 to 16,
   $\text{—}NHCO(CH_2)_2CH(COOH)NH\text{—}CO(CH_2)_qCH_3$, wherein q is an integer from 10 to 16,
   $CH_3(CH_2)_nCH(COOH)NHCO\text{—}$, wherein n is an integer from 9 to 15,
   $CH_3(CH_2)_pNHCO\text{—}$, wherein p is an integer from 10 to 18,
   $\text{—}CONHCH(COOH)(CH_2)_4NH\text{—}CO(CH_2)_mCH_3$, wherein m is an integer from 8 to 18,
   $\text{—}CONHCH(COOH)(CH_2)_4NH\text{—}COCH((CH_2)_2COOH)NH\text{—}CO(CH_2)_pCH_3$, wherein p is an integer from 10 to 16,
   $\text{—}CONHCH(COOH)(CH_2)_4NH\text{—}CO(CH_2)_2CH(COOH)NH\text{—}CO(CH_2)_qCH_3$, wherein q is an integer from 10 to 16, and a partly or completely hydrogenated cyclopentanophenanthrene skeleton.

12. A peptide as claimed in claim 9 wherein the lipophilic group-containing side chain is a $C_{12}$, $C_{14}$, $C_{16}$ or $C_{18}$ acyl group acylating an amino group present in the side chain of a residue of the backbone of the peptide.

13. A peptide as claimed in claim 10 wherein the side chain comprises a tetradecanoyl group acylating an amino group present in the side chain of a residue of the backbone of the peptide.

14. A peptide as claimed in claim 8 wherein the lipophilic group-containing side chain is formed by acylation of the epsilon amino group of a Lys13 substitution in the peptide.

15. A peptide as claimed in claim 6 which comprises a side chain to the backbone of the peptide, wherein the side chain comprises a GAG binding motif.

16. A peptide as claimed in claim 15 wherein the GAG-binding motif comprises one or more of the amino acid sequences XBBXBX (SEQ ID NO:13) and XBBBXXBX (SEQ ID NO:14), wherein B is a basic amino acid residue and X is any amino acid residue.

17. A peptide as claimed in claim 15 wherein the GAG-binding motif is concatameric or dendrimeric.

18. A peptide as claimed in claim 15 wherein the GAG-binding motif is Ala-Arg-Arg-Arg-Ala-Ala-Arg-Ala-Ala-Arg-Arg-Arg-Ala-Ala-Arg-Ala (SEQ ID NO:7) coupled through an amide bond formed between the C-terminus of the concatameric GAG-binding motif and the epsilon amino group of a Lys13 substitution in the peptide.

19. The peptide as claimed in claim 15 wherein the GAG-binding motif is Ala-Arg-Arg-Arg-Ala-Ala-Arg-Ala-Ala-Arg-Arg-Arg-Ala-Ala-Arg-Ala-Ala-Arg-Arg-Arg-Ala-Ala-Arg-Ala (SEQ ID NO:8) coupled through an amide bond formed between the C-terminus of the concatameric GAG-binding motif and the epsilon amino group of a Lys13 substitution in the peptide.

20. A peptide as claimed in claim 6 which comprises the GAG binding motif, wherein the GAG binding motif is covalently linked to the C- or N-terminus of the peptide, either directly or via a linker radical.

21. A peptide as claimed in claim 20 wherein the GAG binding motif is covalently linked either directly or via a linker radical to the N-terminus of the peptide.

22. A peptide as claimed in claim 20 wherein the GAG-binding motif comprises one or more of the amino acid sequences XBBXBX (SEQ ID NO:13) and XBBBXXBX (SEQ ID NO:14), wherein B is a basic amino acid residue and X is any amino acid residue.

23. A peptide as claimed in claim 19 wherein the GAG-binding motif comprises the amino acid sequence [XBBBXXBX (SEQ ID NO:14)]$_n$, where n is 1 to 5, B is a basic amino acid residue and X is any amino acid residue.

24. A peptide as claimed in claim 15 wherein the GAG binding motif is an (Ala-Arg-Arg-Arg-Ala-Ala-Ala-Arg-Ala)$_3$ (SEQ ID NO:10) acylation of the epsilon amino group of a Lys13 substitution in the peptide.

25. A peptide as claimed in claim 6 PEGylated with a PEG which is a polyethylene glycol or a polyethylene oxide having a molecular weight of at the most about 20 kDa.

26. A peptide as claimed in claim 6 which is a PEG adduct on the epsilon amino group of a Lys13 substitution in the peptide.

27. A peptide as claimed in claim 6 which comprises a helix inducing motif which is covalently linked, either directly or via a linker radical, to the C- or N-terminus of the peptide.

28. A peptide as claimed in claim 27 wherein the helix inducing peptide is covalently linked, either directly or via a linker radical, to the N-terminus of the peptide.

29. A peptide as claimed in claim 27 wherein the helix inducing motif comprises 4-20 amino acid residues selected from the group consisting of Ala, Leu, Ser, Thr, Tyr, Asn, Gln, Asp, Glu, Lys, Arg, His, Met, Orn, and amino acid residues of formula —NH—C(R1)(R2)-CO— wherein R1 is hydrogen and R2 is optionally substituted C1-C6 alkyl, phenyl or phenylmethyl, or R1 and R2 taken together with the C atom to which they are attached form a cyclopentyl, cyclohexyl or cycloheptyl ring.

30. A peptide as claimed in claim 27 wherein the helix inducing motif comprises 4, 5 or 6 Lys residues.

31. A peptide as claimed in claim 27 which is has an N-terminal Lys-Lys-Lys-Lys-Lys-Lys-Lys (SEQ ID NO:12) sequence.

32. A pharmaceutical composition comprising one or more peptides as claimed in claim 1 together with a pharmaceutically acceptable excipient.

33. A cosmetic composition comprising one or more peptides as claimed in claim 1 together with a cosmetically acceptable excipient.

34. The peptide of claim 4 which comprises an N-terminal N-(N'-tetradecanoyl)-gammaglutamoyl group.

35. The peptide of claim 1 which consists of the amino acid sequence SEQ ID NO:4.

36. The pharmaceutical composition of claim 32 wherein the peptide consists of the amino acid sequence SEQ ID NO:4.

37. The cosmetic composition of claim 33 wherein the peptide consists of the amino acid sequence SEQ ID NO:4.

* * * * *